(12) United States Patent
Deuel et al.

(10) Patent No.: US 12,364,471 B2
(45) Date of Patent: Jul. 22, 2025

(54) ENDOSCOPIC SUTURING CONTROL HANDLE

(71) Applicant: Boston Scientific Scimed, Inc., Maple Grove, MN (US)

(72) Inventors: Christopher R. Deuel, Melrose, MA (US); Shaun D. Comee, Fiskdale, MA (US); Kevin Windheuser, Hopkinton, MA (US); Todd M. Pfizenmaier, Worcester, MA (US); Andrew Jones, Roslindale, MA (US); Brian H. Yoo, Arlington, MA (US); Evan H. Williams, Cambridge, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1142 days.

(21) Appl. No.: 16/446,292

(22) Filed: Jun. 19, 2019

(65) Prior Publication Data

US 2019/0380562 A1    Dec. 19, 2019

Related U.S. Application Data

(60) Provisional application No. 62/848,853, filed on May 16, 2019, provisional application No. 62/794,075, (Continued)

(51) Int. Cl.
*A61B 17/062* (2006.01)
*A61B 1/00* (2006.01)
(Continued)

(52) U.S. Cl.
CPC ...... *A61B 17/0625* (2013.01); *A61B 1/00066* (2013.01); *A61B 1/0008* (2013.01);
(Continued)

(58) Field of Classification Search
CPC ............ A61B 17/0469; A61B 1/00066; A61B 1/00131; A61B 1/00133; A61B 1/018; A61B 1/0008; A61B 10/04
See application file for complete search history.

(56) References Cited

U.S. PATENT DOCUMENTS

| 5,910,105 A | 6/1999 | Swain et al. |
| 7,927,271 B2 | 4/2011 | Dimitriou et al. |
| (Continued) | | |

FOREIGN PATENT DOCUMENTS

| JP | 2003265406 A | 9/2003 |
| WO | 0018463 A1 | 4/2000 |
| WO | 2004021868 A2 | 3/2004 |

OTHER PUBLICATIONS

International Search Report and Written Opinion for International Application No. PCT/US2019/03008, mailed on Oct. 1, 2019, 13 pages.

(Continued)

*Primary Examiner* — Melanie R Tyson
*Assistant Examiner* — Mikail A Mannan
(74) *Attorney, Agent, or Firm* — Seager, Tufte & Wickhem, LLP

(57) ABSTRACT

The present disclosure relates generally to the field of medical devices. In particular, the present disclosure relates to medical devices, systems and methods to endoscopically suture or otherwise manipulate tissues, organs and/or structures within a body of a patient.

20 Claims, 10 Drawing Sheets

Related U.S. Application Data filed on Jan. 18, 2019, provisional application No. 62/686,923, filed on Jun. 19, 2018.

(51) Int. Cl.
*A61B 1/018* (2006.01)
*A61B 10/04* (2006.01)
*A61B 17/00* (2006.01)
*A61B 17/04* (2006.01)
*A61B 17/06* (2006.01)

(52) U.S. Cl.
CPC ...... *A61B 1/00131* (2013.01); *A61B 1/00133* (2013.01); *A61B 1/018* (2013.01); *A61B 10/04* (2013.01); *A61B 17/0469* (2013.01); *A61B 17/0482* (2013.01); *A61B 2017/0034* (2013.01); *A61B 2017/00367* (2013.01); *A61B 2017/0042* (2013.01); *A61B 2017/00424* (2013.01); *A61B 17/06166* (2013.01)

(56) References Cited

U.S. PATENT DOCUMENTS

| | | |
|---|---|---|
| 8,795,325 B2 | 8/2014 | Taylor et al. |
| 10,932,771 B2 | 3/2021 | Comee et al. |
| 2010/0125164 A1 | 5/2010 | Labombard |
| 2012/0271327 A1 | 10/2012 | West et al. |
| 2014/0190305 A1* | 7/2014 | Okamoto ................. B25J 18/06 901/21 |
| 2015/0342445 A1* | 12/2015 | Jones ................. A61B 1/00133 600/106 |
| 2016/0089014 A1* | 3/2016 | Oskin .................... A61B 1/307 604/517 |
| 2016/0367231 A1* | 12/2016 | Uemichi ............. A61B 1/00133 |
| 2017/0035277 A1* | 2/2017 | Kucharski ................ A61B 1/05 |
| 2017/0265723 A1* | 9/2017 | Yamaya ............. A61B 1/00096 |
| 2018/0160885 A1 | 6/2018 | Abitbol |
| 2019/0380701 A1 | 12/2019 | Deuel et al. |
| 2021/0106323 A1 | 4/2021 | Comee et al. |

OTHER PUBLICATIONS

International Search Report and Written Opinion for International application No. PCT/US2019/038008, mailed on Oct. 1, 2019, 13 pages.

* cited by examiner

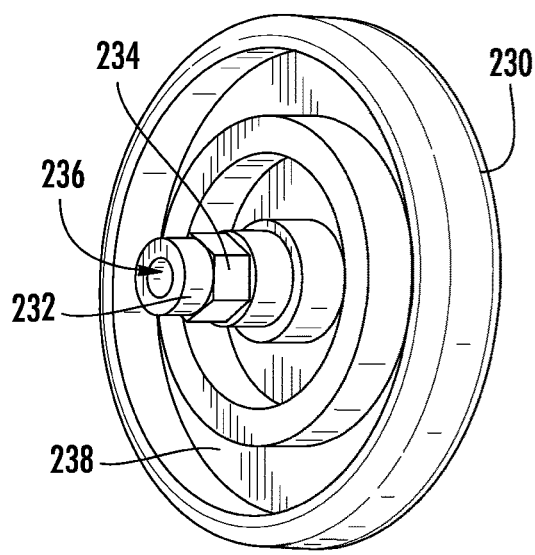 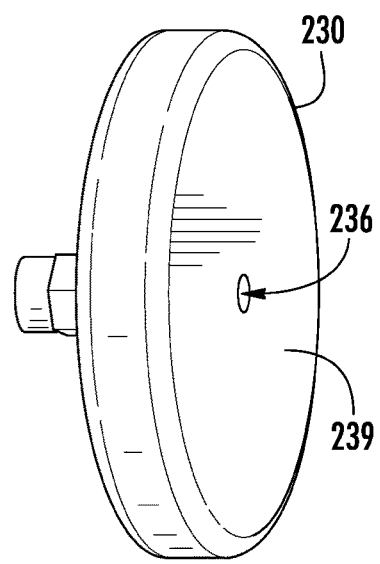
FIG. 7A  FIG. 7B
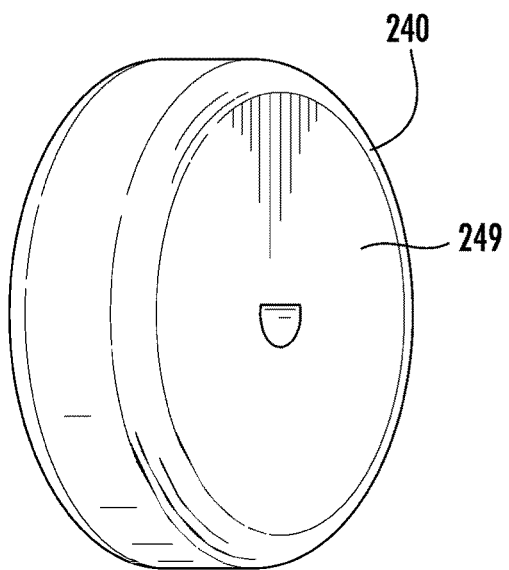 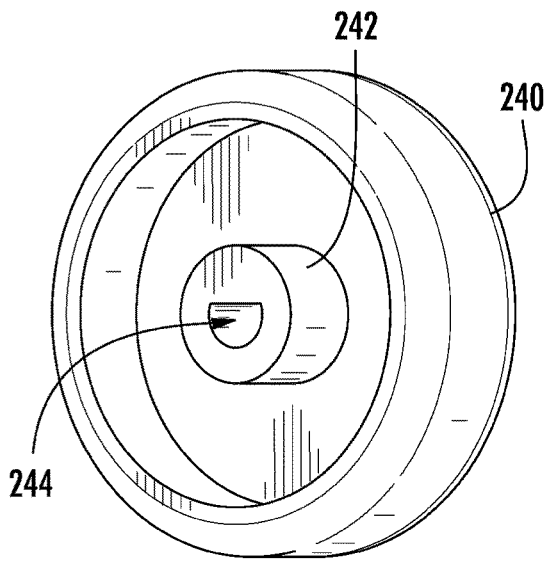
FIG. 8A  FIG. 8B
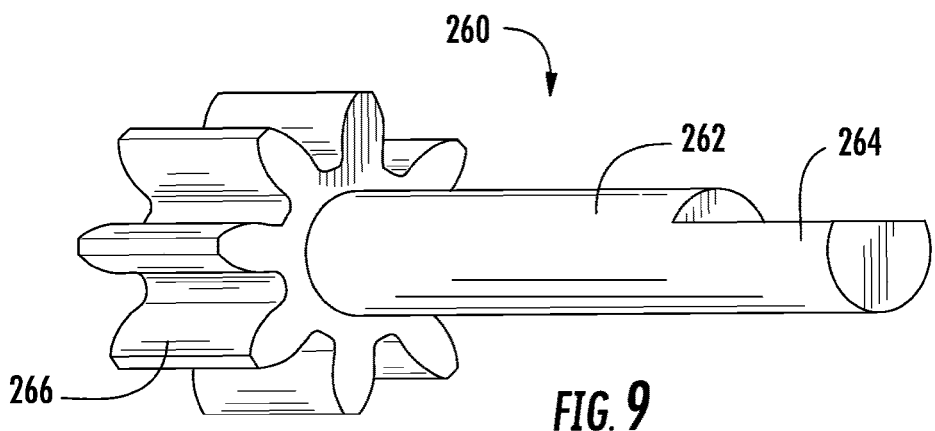
FIG. 9

ENDOSCOPIC SUTURING CONTROL HANDLE

CROSS REFERENCE TO RELATED APPLICATIONS

This application claims the benefit of priority under 35 U.S.C. § 119 to U.S. Provisional Patent Application Ser. No. 62/794,075, filed on Jan. 18, 2019, titled "Endoscopic Suturing Control Handle;" U.S. Provisional Patent Application Ser. No. 62/848,853, filed on May 16, 2019, titled "Control Handle for Endoscopic Suturing;" and U.S. Provisional Patent Application Ser. No. 62/686,923, filed on Jun. 19, 2018, titled "Endoscopic Handle Attachment For Use With Suture Based Closure Device;" each of which are incorporated by reference in their entireties herein for all purposes.

FIELD

The present disclosure relates generally to the field of medical devices. In particular, the present disclosure relates to medical devices, systems and methods to endoscopically suture or otherwise manipulate tissues, organs and/or structures within a body of a patient.

BACKGROUND

A variety of endoscopic instruments are commonly deployed through the working channel of an endoscope for diagnostic and/or therapeutic purposes. Non-limiting examples of such endoscopic instruments may include tissue graspers, suturing devices, hemostatic clips, snares, baskets, scissors, electrosurgical knives and the like. More complicated medical procedures may require one or more additional endoscopic instruments to be used and/or manipulated simultaneously. In some instances, the additional endoscopic instrument(s) may extend through the lumen of a tubular member attached to or extending alongside an outer surface of the endoscope. Each additional endoscopic instrument generally includes a separate control handle that is not fastened to the handle of the endoscope due to the lack of an appropriate attachment device. Although a medical assistant(s) may readily manipulate one or more of the additional endoscopic instrument(s) remotely, single-user control of multiple endoscopic instrument(s) that are not attached to the endoscope handle tends to be cumbersome and inefficient.

A variety of advantageous medical outcomes may therefore be realized by the devices, systems and/or methods of the present disclosure, which provide in part a control handle that securely attaches to an outer surface of an endoscope handle to allow single user control of one or more endoscopic instruments in an efficient and non-cumbersome manner.

SUMMARY

In one aspect, the present disclosure relates to a control handle that may comprise an adapter configured to attach to an outer surface of an endoscope, a housing comprising a drive wheel and an idler wheel, a lever pivotally connected to the housing, the lever configured to move between a first position and a second position to rotate the drive wheel and the idler wheel, and a guide movably disposed within the housing. The guide may comprise a shaft and a lumen extending through the shaft, wherein the lumen may substantially align with a space between the drive wheel and the idler wheel. The adapter may include a curved inner surface configured to conform to the outer surface of the endoscope. The adapter may include one or more attachment elements configured to reversibly engage the outer surface of the endoscope. A proximal portion of the adapter may include a channel configured to receive a biopsy port of the endoscope. The adapter may include a first arm with a first attachment point. The first attachment point may be configured to receive an outer surface of an endoscopic instrument. The adapter may include a second arm with a second attachment point. The second attachment point may be configured to receive a proximal end of a tubular member. The drive wheel may be pinned to a drive gear and the idler wheel may be pinned to an idler gear. Teeth of the drive gear may mate with corresponding teeth of the idler gear. The lever may be pivotally connected to the drive wheel and the drive gear. Moving the lever from the first position to the second position may rotate the drive wheel and the drive gear in a first direction and may rotate the idler wheel and idler gear in a second direction. Moving the lever from the second position to the first position may rotate the drive wheel and the drive gear in the second direction and may rotate the idler wheel and idler gear in the first direction. The idler wheel and idler gear may be rotatably mounted on opposite sides of an idler. The idler may be spring-loaded within the housing.

In one aspect, the present disclosure relates to an endoscopic system that may comprise a control handle attached to an endoscope. The control handle may comprise an adapter configured to attach the control handle to the endoscope, a housing comprising a drive wheel and an idler wheel, a lever pivotally connected to the housing, the lever configured to move between a first position and a second position to rotate the drive wheel and the idler wheel, and a guide movably disposed within the housing. The guide may comprise a shaft and a lumen extending through the shaft. The lumen may substantially align with a space between the drive wheel and the idler wheel. The system may further include a first endoscopic instrument comprising a flexible catheter defining a lumen, a control wire movably disposed within the lumen of the flexible catheter, and a suturing device disposed at a distal end of the first endoscopic instrument. The suturing device may comprise a shuttle attached to the distal end of the flexible catheter, a sleeve attached to a distal end of the control wire, and a suturing needle attached to the shuttle. A proximal portion of the control wire may extend beyond the proximal end of the flexible catheter and the lever. A proximal end of the control wire may be attached to a dial at a proximal end of the lever. The drive wheel may be pinned to a drive gear and the idler wheel may be pinned to an idler gear, wherein teeth of the drive gear may mate with corresponding teeth of the idler gear. The lever may be pivotally connected to the drive wheel and the drive gear. Moving the lever from the first position to the second position may rotate the drive wheel and the drive gear in a first direction and may rotate the idler wheel and idler gear in a second direction. Moving the lever from the second position to the first position may rotate the drive wheel and the drive gear in the second direction and may rotate the idler wheel and idler gear in the first direction. The drive wheel and idler wheel may contact opposite sides of the flexible catheter extending through the housing. Moving the lever from the first position to the second position may distally advance the flexible catheter within the working channel of the endoscope. Moving the lever from the second position to the first position may proximally retract the flexible catheter within the working channel of the endoscope. A tab may be slidably disposed along a length of the lever. Rotating the dial in a first direction may distally advance the tab along the lever to distally advance the control wire within the flexible catheter. Rotating the dial in a second direction may proximally retract the tab along the lever to proximally retract the control wire within the flexible catheter. A proximal end of the flexible catheter may be attached to a distal end of the tab. The flexible catheter may extend from the distal end of the tab, through the lumen of the shaft, through the housing between the drive wheel and idler wheel and through a working channel of the endoscope. The sleeve may be proximally retracted relative to the flexible catheter as the control wire is distally extended within the flexible catheter. The sleeve may be distally advanced relative to the flexible catheter as the control wire is proximally retracted within the flexible catheter. The needle may be exposed from within the sleeve when the control wire is distally extended. The needle may be retracted within the sleeve when the control wire is proximally retracted.

In one aspect, the present disclosure relates to a method of suturing tissue that may comprise inserting an endoscope into a body passage of a patient, advancing a first endoscopic instrument through a working channel of the endoscope to position a suturing device disposed at a distal end of the endoscopic instrument adjacent to a tissue of the body passage, and actuating the suturing device using a control handle attached to the endoscope to puncture the tissue of the body passage. The control handle may comprise a housing comprising a drive wheel and an idler wheel, a lever pivotally connected to the housing, the lever configured to move between a first position and a second position to rotate the drive wheel and the idler wheel, and a guide movably disposed within the housing. The guide may comprise a shaft and a lumen extending through the shaft. The lumen may substantially align with a space between the drive wheel and the idler wheel. Actuating the suturing device may include moving the lever from the first position to the second position to distally advances the first endoscopic instrument within the working channel of the endoscope. Actuating the suturing device may include moving the lever from the second position to the first position to proximally retract the first endoscopic instrument within the working channel of the endoscope.

In one aspect, the present disclosure relates to a control handle that may comprise an adapter configured to reversibly attach to an outer surface of an endoscope handle. The control handle may include a shaft attached to the adapter. The adapter may include a channel configured to receive a biopsy port and/or biopsy cap of the endoscope handle. A lumen may extend through a full length of the shaft to receive a proximal portion of a first endoscopic instrument therethrough. A first wheel and a second wheel may be rotatably attached to a proximal end of the shaft. A housing may be attached to the proximal end of the shaft opposite the first and second wheels. A linear gear may be slidably/movably disposed within housing. A proximal portion of a first endoscopic instrument may extend through the lumen of the shaft and the biopsy port into the working channel of the endoscope handle. The first endoscopic instrument may include a flexible catheter defining a lumen and a control wire movably/slidably disposed within the lumen through a full length of the flexible catheter. A suturing device may be disposed at a distal end of the first endoscopic instrument. The control wire may be moved proximally and distally within the flexible catheter such that movement of the sleeve in a proximal direction may expose the suturing needle from within the sleeve, and movement of the sleeve in a distal direction may cover the suturing needle within the sleeve. A drive wheel and idler wheel may be rotatably disposed within the control handle and configured to firmly contact opposite sides of the flexible catheter. The first wheel may include an inner surface and an outer surface. A post comprising a polygonal outer surface may extend from the inner surface. A lumen may extend through the post to the outer surface of the first wheel. The polygonal outer surface may be configured to contact a corresponding polygonal surface of the drive wheel such that the first wheel may be rotated in a first direction to simultaneously rotate the drive wheel in a first direction and the idler wheel in a second direction opposite the first direction. The first wheel may also be rotated in a second direction to simultaneously rotate the drive wheel in a second direction and the idler wheel in a first direction opposite the second direction. The second wheel may include an inner surface and an outer surface. A tab defining an opening may extend from the inner surface of the second wheel. The tab may include a substantially circular outer surface configured to be rotatably disposed within the lumen extending through the outer surface of the first wheel. The opening of the tab may include a non-spherical shape configured to receive the keyed end of a pinion shaft. The first and second wheels may be rotatably attached to the proximal end of the shaft by a pinion shaft. The pinion shaft may include a substantially round portion, a keyed end and a pinion gear configured to extend into the housing and engage the corresponding teeth of the linear gear. The pinion shaft may extend through the lumen of the first wheel and into the tab of the second wheel such that the substantially round portion of the pinion shaft may be disposed within the lumen of the first wheel and the keyed end may extend into the opening of the second wheel. The first wheel may be rotated in a first direction and a second direction around the substantially round portion of the pinion shaft independent of the second wheel. The second wheel may be rotated in a first direction and second direction such that the substantially round portion and pinion gear of the pinion shaft may rotate in a corresponding first or second direction independent of the first wheel. A distal end of the linear gear may be attached to the proximal end of the flexible catheter, and a proximal portion of the flexible catheter may form a loop to extend from the distal end of the linear gear into/through the lumen of the shaft. A proximal portion of the control wire may extend through the housing and the linear gear. A proximal end of the control wire may be connected to a dial or knob at the proximal end of the housing. The dial or knob may include a threaded inner surface configured to engage corresponding threaded grooves on an outer surface of the proximal end the housing. The dial or knob may be rotated in a first direction or second direction to move the control wire proximally or distally and in turn move the linear gear proximally or distally along the housing.

In one aspect, the present disclosure relates to a control handle that may comprise an adapter configured to reversibly attach to an outer surface of an endoscope handle. The adapter may include a channel configured to receive a biopsy port and/or biopsy cap of the endoscope handle. The control handle may include a shaft attached to the adapter. A proximal end of the shaft may be attached to a first surface of a base. An inner post may extend through an opening formed within a second surface of the base. A lumen may extend through a full length of the inner post and substantially align with a corresponding lumen extending through a full length of the shaft. An outer surface of the inner post may include a groove extending along a portion of a length of the inner post. An arm may extend outwardly from a distal end of the inner post. A tab may extend from a surface of the arm and substantially parallel to a distal portion of the inner post. The arm may engage a housing slidably/movably disposed within the base. An outer post may be slidably disposed over the inner post. A proximal end of the outer post may include an opening configured to substantially align with the lumen of the inner post and/or firmly engage or grip an outer surface of a flexible catheter extending therethrough. An elevated or raised ridge may be formed along all or a portion of an inner surface of the outer post to engage the corresponding groove of the inner post in an interlocking or keyed-fit configuration. The keyed-fit interaction may allow the outer post to move proximally and distally relative to the inner post without imparting any corresponding proximal or distal movement to the inner post. The keyed-fit interaction may also allow the outer post to be rotated in a first direction and a second direction such that the inner post may rotate in a corresponding first or second direction along with the outer post to move the housing within the base. A proximal end of the flexible catheter may be attached to a sidewall of the base, and a proximal portion of the flexible catheter may form a loop to extend from the base into/through the opening of the outer post, through the respective lumens of the inner post and shaft and into a working channel of the endoscope. A proximal portion of the control wire may extend through an opening in the sidewall of the base and a proximal end of the control wire may be connected to the housing. The outer and inner posts may be rotated in the first direction or second direction to move the housing within the base and in turn move the control wire proximally or distally within the flexible catheter. A suturing device may be disposed at a distal end of a first endoscopic instrument. The control wire may be moved proximally and distally within the flexible catheter such that movement of the sleeve in a proximal direction may expose the suturing needle from within the sleeve, and movement of the sleeve in a distal direction may cover the suturing needle within the sleeve.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 7A-7B provide perspective views of a wheel of the control handle of FIG. 6, according to one embodiment of the present disclosure.

FIGS. 8A-8B provide perspective views of a wheel of the control handle of FIG. 6, according to one embodiment of the present disclosure.

FIG. 9 provides a perspective view of a pinion shaft of the control handle of FIG. 6, according to one embodiment of the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to medical devices, systems and methods for manipulating a suturing needle with a control handle attached to the handle of an endoscope, it should be appreciated that such devices, systems and methods may be used to manipulate a variety of endoscopic instruments to treat, manipulate, diagnose and/or observe a variety of tissues, organs, anatomical structures, body lumens, body passages and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

Figure 1:
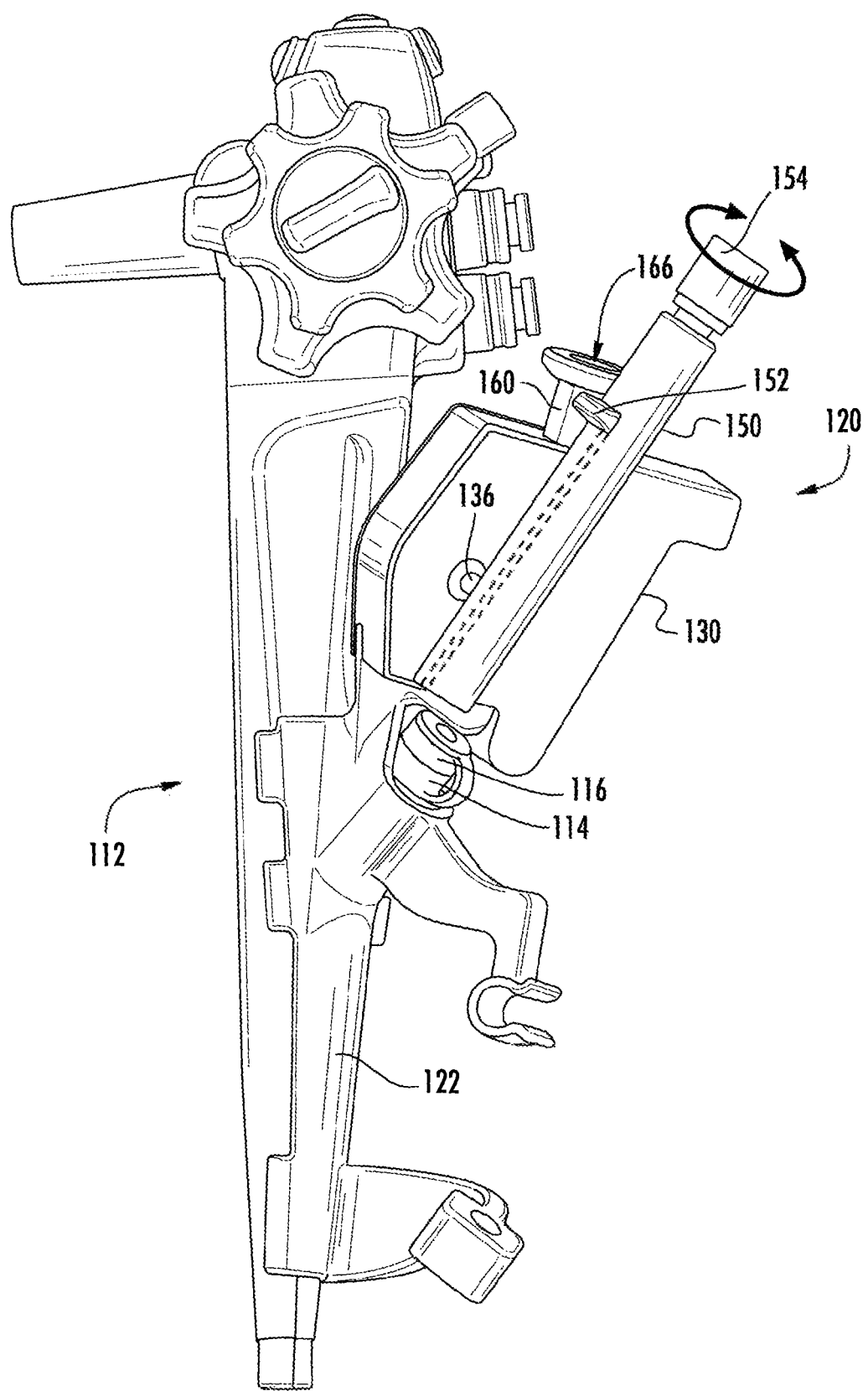
FIG. 1 provides a perspective view of a control handle attached to the outer surface of an endoscope handle, according to one embodiment of the present disclosure.

Referring to FIG. 1, in one embodiment, a control handle 120 (e.g., endoscope handle attachment, endoscope suturing control handle, etc.) of the present disclosure may include an adapter 122 (e.g., grip attachment) configured to reversibly (e.g., removably, releasably, etc.) attach to an outer surface of an endoscope handle 112 (e.g., grip). In various embodiments, the control handle 120 may include a housing 130 attached to (e.g., connected to, integrally formed with, etc.) the adapter 122, a lever 150 pivotally connected to the housing 130, a tab 152 slidably disposed along a length of the lever 150 and a guide 160 (e.g., lock/release mechanism) movably (e.g., slidably) disposed within (e.g., extending through) an opening formed within the housing 130 (e.g., the opening may be formed within an upper or top portion of) the housing. The housing 130 may include geared rollers comprising a drive wheel 132 and an idler wheel 134 (FIG. 4A) configured to firmly contact opposite sides of a flexible catheter of a first endoscopic instrument extending between the drive wheel 132 and idler wheel 134. The lever 150 may be configured to move back-and-forth between a first position (e.g., back) and a second position (e.g., forward) to control the direction of rotation (e.g., clockwise and counterclockwise) of the drive wheel 132 and idler wheel 134. The guide 160 may be movably disposed within the top portion of the housing 130 such that a lumen 166 extending through a shaft 162 (FIG. 4) of the guide 160 substantially aligns with a space between the drive wheel 132 and the idler wheel 134. A bottom portion of the housing 130 may include an opening (not shown) configured to align with the biopsy port 114 and biopsy cap 116 of the endoscope handle 112.

Figure 2:
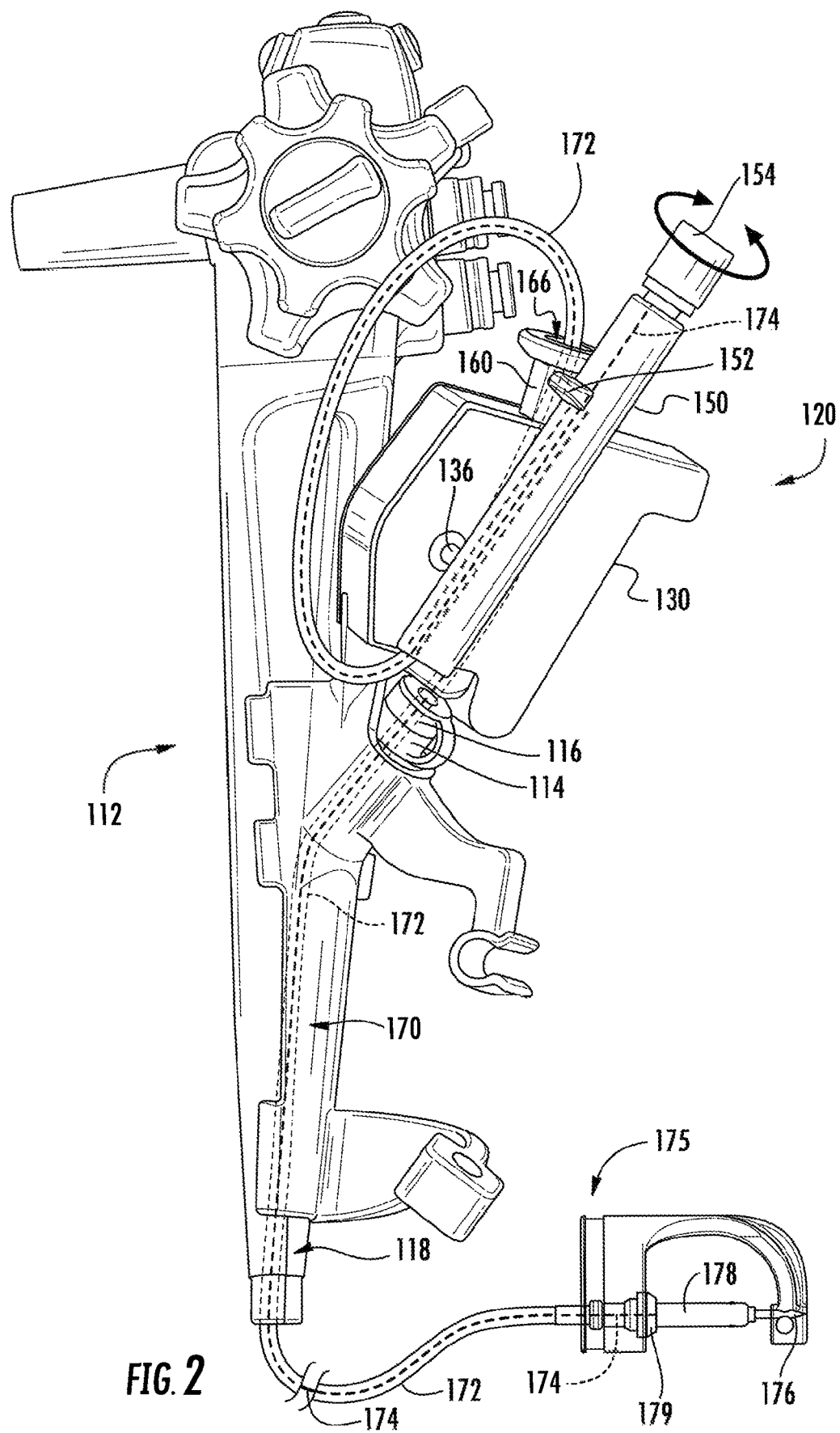
FIG. 2 provides a perspective view of an endoscopic instrument extending through a control handle and working channel of an endoscope, according to one embodiment of the present disclosure.

Referring to FIG. 2, in one embodiment, a proximal portion of a first endoscopic instrument 170 may extend through the lumen 166 of the guide 160, into the housing 130 through the space between the drive wheel 132 and idler wheel 134, through the opening in the bottom portion of the housing 130 and through the biopsy port 114 into the working channel 118 of the endoscope handle 112. In one embodiment, the first endoscopic instrument 170 may include a flexible catheter 172 (e.g., flexible sheath, flexible coil, etc.) defining a lumen and a control wire 174 movably/slidably disposed within the lumen through a full length of the flexible catheter 172. A suturing device 175 may be disposed at the distal end of the first endoscopic instrument 170. The suturing device 175 may include a shuttle 179 attached (e.g., welded or bonded) to the distal end of the flexible catheter 172 and a sleeve 178 attached (e.g., welded or bonded) to a distal end of the control wire 174. The control wire 174 may be moved proximally and distally within the flexible catheter such that the sleeve 178 moves relative to the flexible catheter 172. A suturing needle 176 may be attached to the shuttle 179 such that movement of the sleeve 178 in a proximal direction exposes the suturing needle 176 from within the sleeve, and movement of the sleeve 178 in a distal direction covers the suturing needle 176 within the sleeve 178. A proximal end of the flexible catheter 172 may be attached to a distal end of the lever 150 such that the manipulation of the lever 150 may move the flexible catheter, and the exposed suturing needle 176 attached thereto, proximally or distally.

Figure 3A:
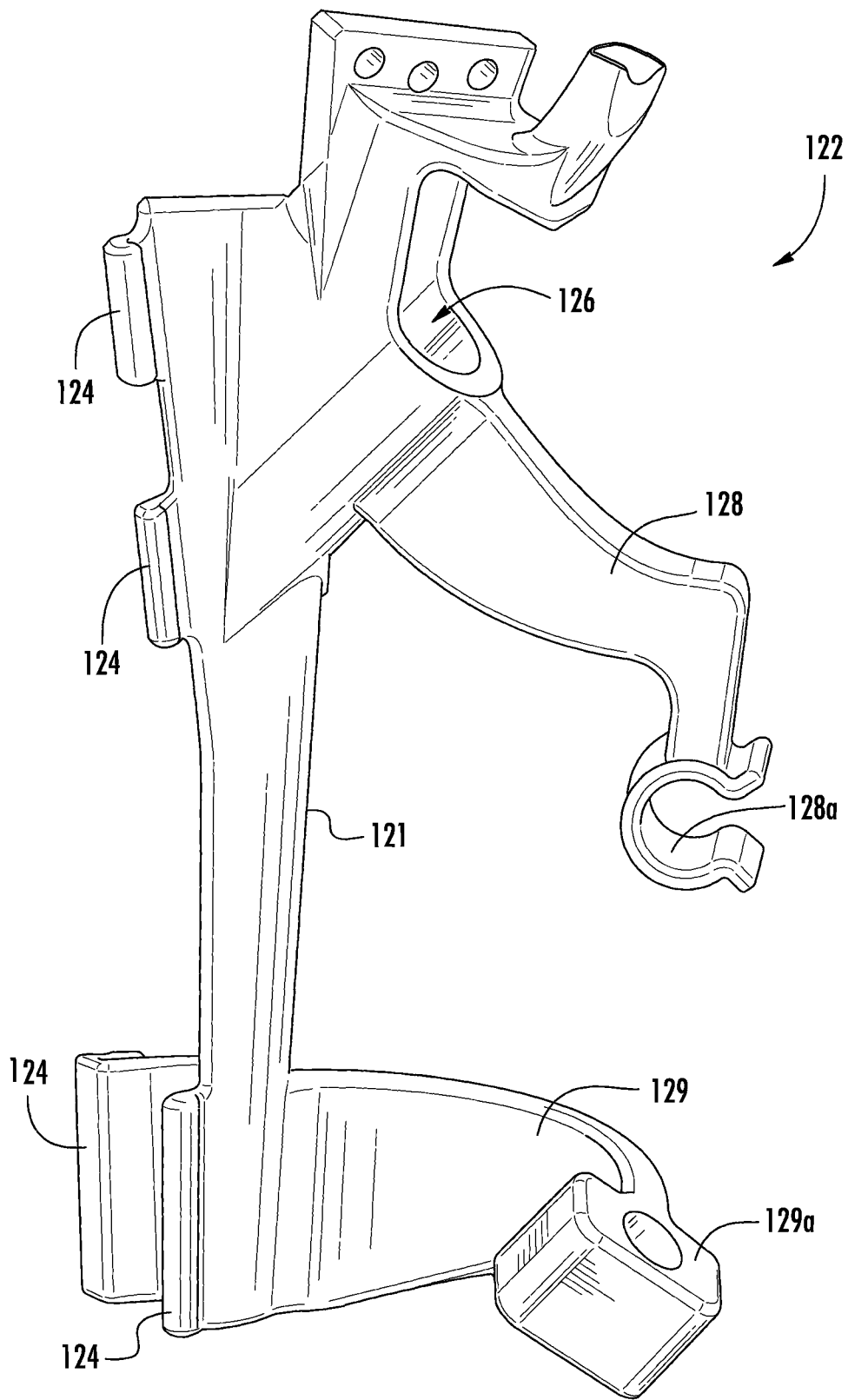
FIGS. 3A-3B provide perspective views of an adapter of a control handle, according to one embodiment of the present disclosure.
Figure 3B:
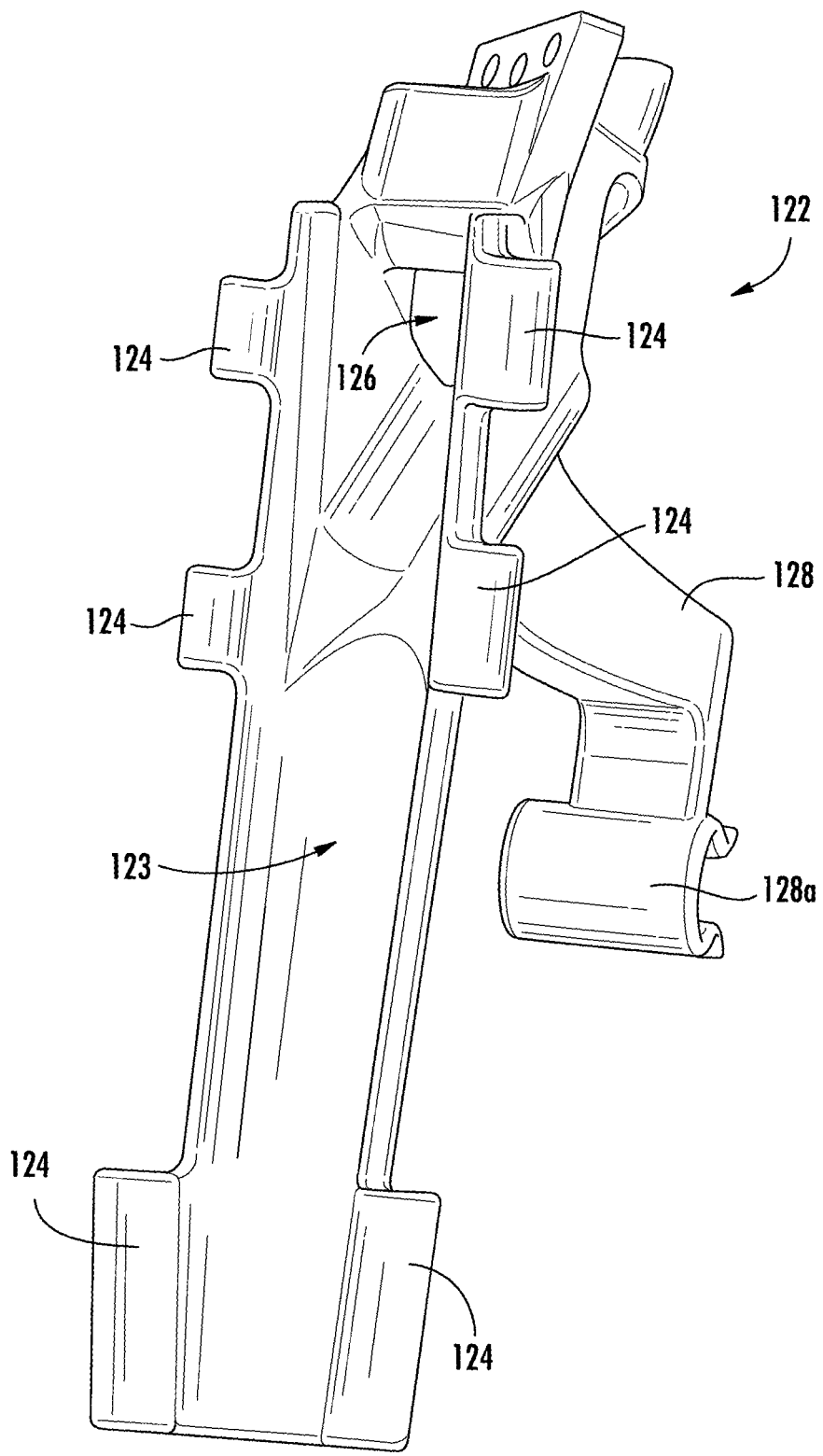

Referring to FIGS. 3A-3B, in one embodiment, an adapter 122 of the control handle 120 may include a backbone 121 with curved inner surface 123 configured to conform to (e.g., receive, match, etc.) the corresponding outer surface of an endoscope handle. In various embodiments, the curved inner surface 123 may be configured to match the corresponding tapered design of a standard endoscope handle. The backbone 121 may include one or more attachment elements 124 (e.g., tabs, hooks, clips, projections, etc.) configured to reversibly engage (e.g., via a snap-fit, interference fit, etc.) the outer surface of an endoscope handle at one or more locations. The attachment elements 124 may vary depending on the dimensions and other characteristics of the particular endoscope handle, but as an illustrative and non-limiting example, a pair of attachment elements 124 may include corresponding curved or hooked ends on opposing sides of the backbone 121. In various embodiments, one or more quick release elements (e.g., O-rings, rubber bands, elastic members, etc.) may engage the opposing curved or hooked ends to further secure the adapter 122 to the endoscope handle.

In one embodiment, a channel 126 (e.g., opening) may extend through a proximal portion of the backbone 121 to receive (e.g., accommodate, fit over, etc.) a biopsy port 114 and/or biopsy cap 116 of an endoscope handle. In various embodiments, the adapter 122 may include a first arm 128 (e.g., upper/primary arm) with a first attachment point 128a attached to or integrally formed with a proximal portion of the backbone 121 and a second arm 129 (e.g., lower/secondary arm) with a second attachment point 129a attached to or integrally formed with a distal portion of the backbone 121. The first attachment point 128a may be configured to reversibly receive the outer surface of a second endoscopic instrument, including, by way of non-limiting example, a tissue grasper, and the second attachment point 129a may be configured to reversibly receive the proximal end of a tubular member. For example, the tubular member may be configured to extend alongside an outer surface of the endoscope and include a lumen through which an additional endoscopic instrument (e.g., the second endoscopic instrument), fluids and the like may be advanced and/or delivered. In various embodiments, the second attachment point 129a may define an opening with a first side (e.g., bottom) of the opening configured to receive a fitting, such as a winged luer fitting, attached to the proximal end of a tubular member. A second side (e.g., top) of the opening of the second attachment point 129a may be configured to receive a valve (e.g., Tuohy Borst valve) through which the second endoscopic instrument may extend through. For example, a luer fitting at the proximal end of a tubular member may be inserted into the second attachment point 129a and a Tuohy Borst valve may be attached to this luer fitting on the first attachment point 128a such that a second medical instrument may be extended through the valve and into/through the tubular member.

In one embodiment, the channel 126 of the adapter 122 may be configured to receive a biopsy port of the endoscope handle 112 such that a first endoscopic instrument may extend into and through the working channel of the endoscope, and a second endoscopic instrument may be attached to the first attachment point 128a of the first arm 128 to extend through the tubular member (e.g., attached to the second attachment point 129a) alongside an outer surface of the endo scope. The first and second endoscopic instruments may be attached to the endoscope handle 112 by the control handle 120 to allow simultaneous and efficient single user control of the first and second endoscopic instruments during a medical procedure.

Although the first attachment point 128a includes a generally C-shaped configuration to provide a snap-fit with the outer surface of a substantially circular second endoscopic instrument, in various embodiments the shape and/or configuration of the first attachment point 128a may vary to reversibly receive the outer surface of a second endoscopic instrument with a variety of sizes and/or shapes. Additional features of the adapter may be found in co-pending U.S. Patent Application 62/686,923, entitled ENDOSCOPIC HANDLE ATTACHMENT FOR USE WITH SUTURE BASED CLOSURE DEVICE, filed concurrently, and is hereby incorporated by reference herein in its entirety.

Figure 4A:
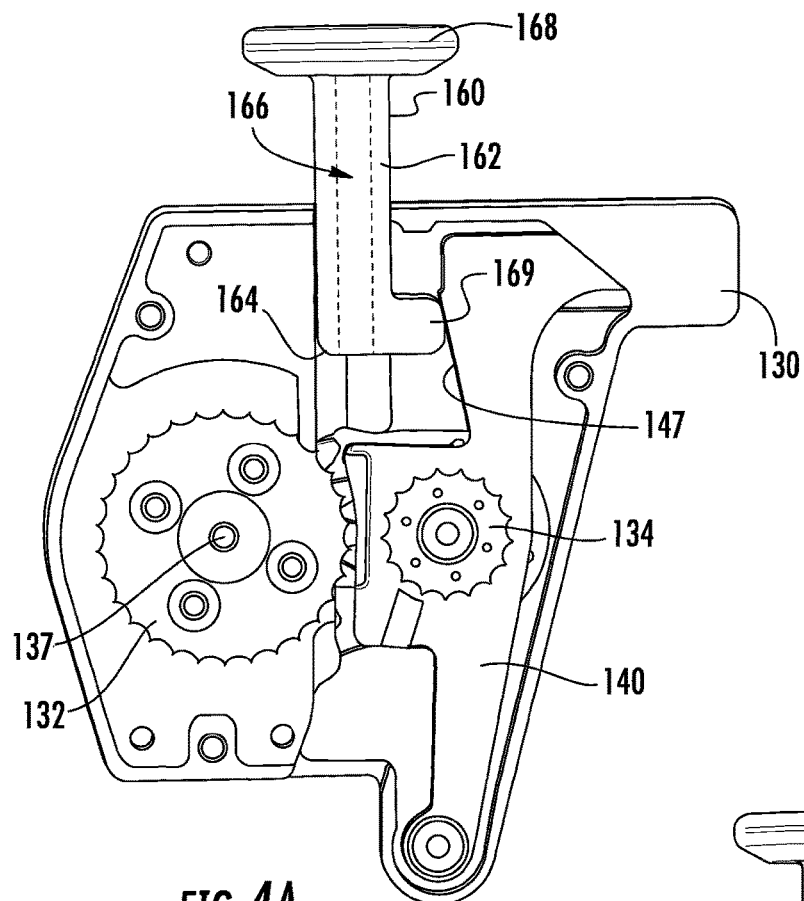
FIGS. 4A-4B provide perspective views of a housing of a control handle housing, according to one embodiment of the present disclosure.
Figure 4B:
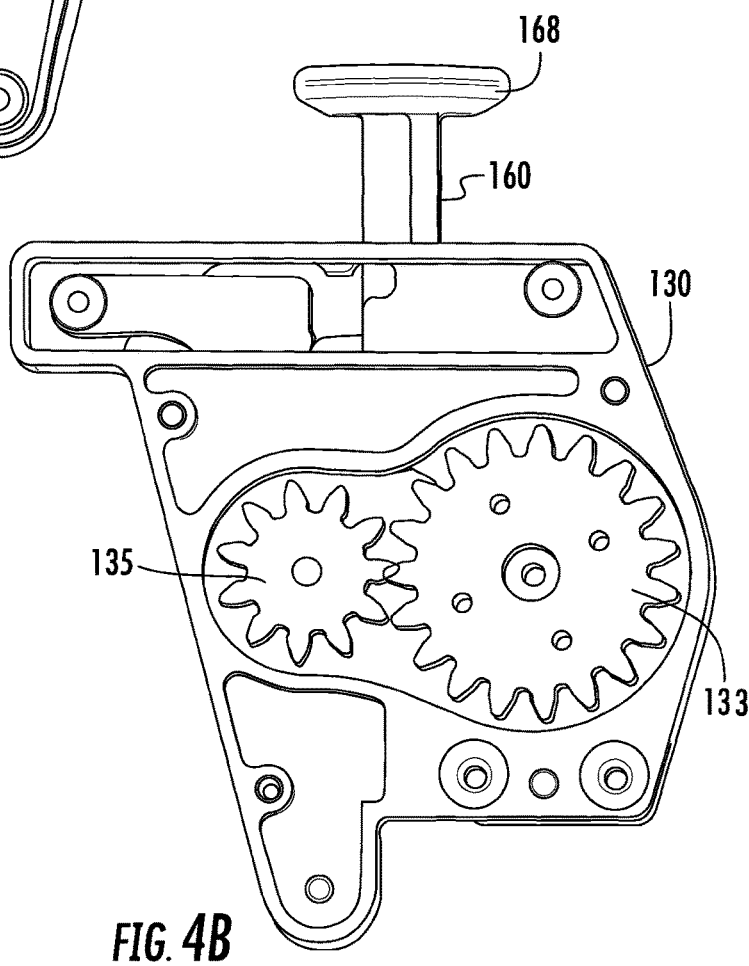

Referring to FIGS. 4A-4B, in one embodiment, a housing 130 of the control handle 120 may include geared rollers comprising a drive wheel 132 and an idler wheel 134. The drive wheel 132 may be pinned (e.g., coupled, attached, etc.) to a drive gear 133 and the idler wheel 134 may be pinned (e.g., coupled, attached, etc.) to an idler gear 135. An opening 137 may extend through an approximate center of the pinned drive wheel 132 and drive gear 133. A pin 136

(e.g., should screw, etc.) (FIG. 1) may extend through the opening 137 to rotatably couple the drive wheel 132 to the drive gear 133. An end of the pin 136 may be attached to an outer surface of the lever 150 to pivotally connect the lever 150 to the housing 130 (FIG. 1). The drive wheel 132 and idler wheel 134 may be separated by a distance (e.g., to firmly contact opposite sides of a flexible catheter of a first endoscopic instrument extending therebetween) and the teeth of the drive gear 133 may interlock/mate with the corresponding teeth of the idler gear 135. The lever 150 may be moved from a first position (e.g., back) to a second position (e.g., forward) to simultaneously rotate the pinned drive wheel 132 and drive gear 133 in a first direction (e.g., counterclockwise) and the pinned idler wheel 134 and idler gear 135 (e.g., via the interlocking teeth of the drive gear 133 and idler gear 135) in a second direction opposite the first direction (e.g., clockwise). The lever 150 may also be moved from the second position to the first position to simultaneously rotate the pinned drive wheel 132 and drive gear 133 in the second direction (e.g., clockwise) and the pinned idler wheel 134 and idler gear 135 (e.g., via the interlocking teeth of the drive gear 133 and idler gear 135) in the second direction opposite the first direction (e.g., counterclockwise).

In one embodiment, the idler wheel 134 and idler gear 135 may be rotatably mounted (e.g., rotatably attached) on opposite sides of an idler 140 (e.g., idler pivot) spring-loaded within the housing 130. The guide 160 (e.g., lock/release) may include a projection 169 (e.g., lip, tab, etc.) extending from a distal end 164 of the shaft 162. The projection 169 may be configured to slidingly engage (e.g., move along) an angled surface 147 of the spring-loaded idler 140 as the guide 160 is moved within the housing 130. For example, a user may grasp a knob 168 (e.g., handle) located at or near a proximal end 163 of the guide 160 and move (e.g., lift) the guide 160 from a first position (e.g., down, locked, etc.) to a second position (e.g., up, unlocked, etc.), thereby moving the projection 169 proximally along the angled surface 147 to move the spring-loaded idler 140, and the idler wheel 134 and idler gear 135 attached thereto, away from the corresponding drive wheel 132 and drive gear 133. With the guide 160 in the second position, a distance between drive wheel 132 and idler wheel 134 may be increased such that a flexible catheter of a first endoscopic instrument is not in firm contact (e.g., direct contact, compressive contact, etc.) with both the drive wheel 132 and the idler wheel 134 and may be loaded through the guide 160 and housing 130 into the biopsy port of the endoscope handle. In addition, with the guide 160 in the second position, the corresponding teeth of the drive gear 133 and idler gear 135 may be removed (e.g., separated) from interlocking contact. A user may also grasp the knob 168 and move (e.g., push, depress, etc.) the guide 160 from the second position to the first position, thereby moving the projection 169 distally along the angled surface 147 to move the spring-loaded idler 140, and the idler wheel 134 and idler gear 135 attached thereto, toward the corresponding drive wheel 132 and drive gear 133. With the guide 160 in the first position, a distance between drive wheel 132 and idler wheel 134 may be decreased such that a flexible catheter of a first endoscopic instrument extending therebetween may be in firm contact with both the drive wheel 132 and the idler wheel 134. In addition, with the guide 160 in the second position, the corresponding teeth of the drive gear 133 and idler gear 135 may be placed in interlocking contact.

As discussed below, with the guide 160 in either the first or second position, a lumen 166 extending through the shaft 162 of the guide 160 may remain in substantial alignment with the space between the drive wheel 132 and the idler wheel 134. With the guide 160 in the second position, the control handle 120 may be in an unlocked configuration in which the drive wheel 132 and idler wheel 134 are not in contact with a flexible catheter of a first endoscopic instrument extending therebetween, e.g., for loading of the first endoscopic tool and/or advancement of the first endoscopic tool through an endoscope and into a body passage of a patient. With the guide 160 in the first position, the control handle 120 may be in an locked configuration in which the drive wheel 132 and idler wheel 134 are in firm contact with opposite sides of a flexible catheter of a first endoscopic instrument extending therebetween, and the teeth of the drive gear 133 and idler gear 135 are interlocked, e.g., for advancing and retracting the endoscopic tool by moving the lever back-and-forth.

Referring again to FIG. 2, in one embodiment, a distal end of the tab 152 may be attached to the proximal end of the flexible catheter 172, and a proximal portion of the flexible catheter 172 may form a loop to extend from the distal end of the tab 152 into/through the guide 160 and housing 130. A proximal portion of the control wire 174 may extend through the lever 150 and the tab 152 and a proximal end of the control wire 174 may be connected to a dial or knob 154 at the proximal end of the lever 150. The dial or knob 154 may include a threaded inner surface configured to engage corresponding threaded grooves on an outer surface of the proximal end of the lever 150. The dial or knob 154 may be rotated in a first direction (e.g., clockwise) or second direction (e.g., counterclockwise) to move the control wire 174 proximally or distally and in turn move the tab 152 proximally or distally along the lever 150. For example, the dial or knob 154 may be rotated in the first direction to move the tab 152 towards the proximal end of the lever 150, and the dial or knob 154 may be rotated in the second direction to move the tab 152 towards the distal end of the lever 150. In various embodiments, the starting position of the tab 152 along the lever 150 may be varied to move the sleeve 178 (e.g., attached to the distal end of the control wire 174) and the flexible catheter 172 (e.g., attached to the shuttle 179 of the suturing device 175) relative to the control wire 174, and thereby move the sleeve 178 relative to the suturing needle 176. For example, as the first endoscopic instrument is advanced through a tortuous body passage, the coils which form the flexible catheter 172 may bend and effectively increase in length as compared to the control wire 174, which does not increase in length upon bending and is effectively pulled back/retracted relative to the flexible catheter 172 to potentially expose the suturing needle 176. In various embodiments, the starting position of the tab 152 along the lever 150 may be varied based on the body passage to be navigated by the endoscope and first endoscopic instrument such that the suturing needle 176 remains covered/protected by the sleeve (e.g., is not exposed) as the flexible catheter 172 bends. With the position of the tab 152 set, and the distal end of the first endoscopic instrument positioned at or near the portion of the body passage to be manipulated, the tab 152 may be extended (e.g., moved distally) along the lever 150 to extend the flexible catheter 172 relative to the control handle 110. For example, as the tab 152 is extended the flexible catheter 172 may "pull" against the control wire 174 to pull the sleeve 178 proximally relative to the flexible catheter 172 to unlock (e.g., expose) the suturing needle 176. The tab 152 may also be retracted (e.g., moved proximally) to lock (e.g., cover) the suturing needle 176 within the sleeve 178, e.g., to reposition and/or remove the first endoscopic instrument.

In use and by way of example, with the guide in the second position, a first endoscopic instrument may be inserted through the lumen of the guide, advanced between the drive wheel and idler wheel and through the biopsy port into the working channel of the endoscope handle. As discussed above, with the guide in the second position, the spring-loaded idler may pivot away from the drive wheel such that the drive wheel and idler wheel do not substantially contact (e.g., are not in firm contact with) the flexible catheter of the first endoscopic instrument and/or the corresponding teeth of the drive gear and drive wheel are not interlocked.

Figure 5A:
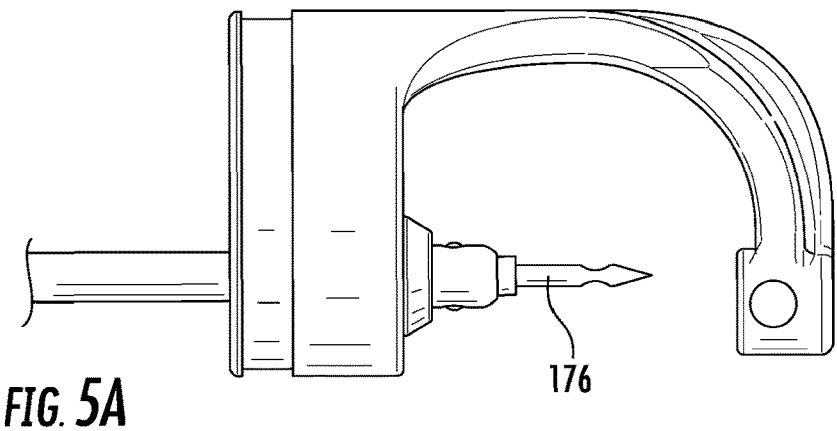
FIGS. 5A-5C provide schematic illustrations of distal end of an endoscopic instrument being manipulated by a control handle, according to one embodiment of the present disclosure.
Figure 5B:
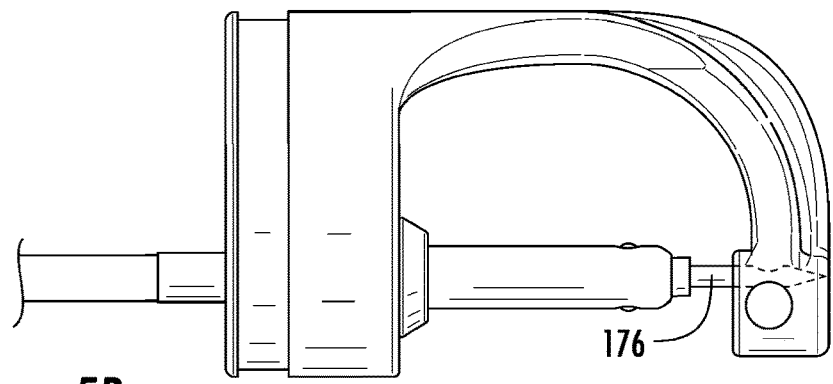
Figure 5C:
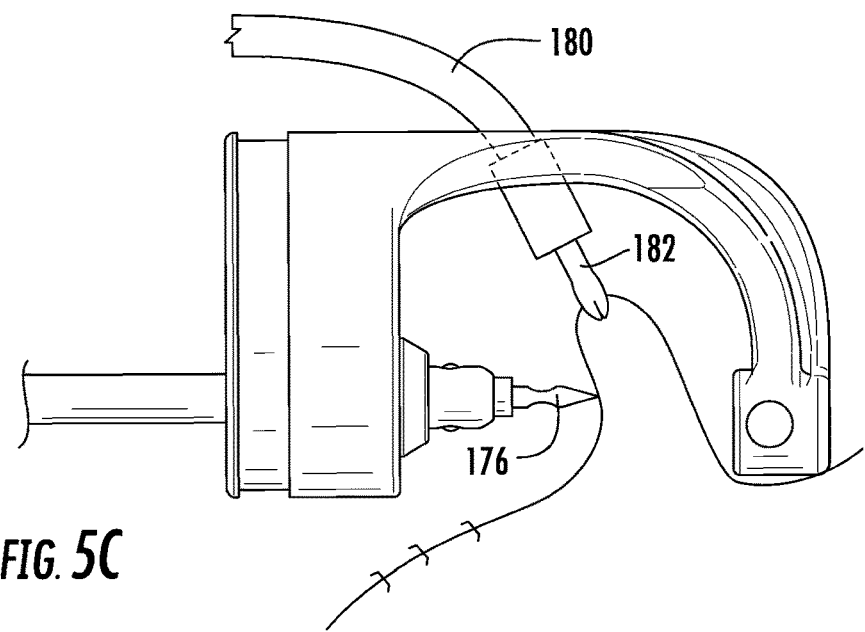

In various embodiments, with the first endoscopic instrument positioned at or near the portion of the body passage to be manipulated, the guide may then be moved from the first position to the second position such that the spring-loaded idler pivots toward the drive wheel to place the drive wheel and idler wheel in firm contact with the flexible catheter of the first endoscopic instrument and/or to place the corresponding teeth of the drive gear and drive wheel in the interlocked configuration. Referring to FIGS. 5A-5C, the tab may then be distally extended to expose the suturing needle 176 at the end of the first endoscopic instrument (FIG. 5A). The lever may then be moved from the first position to the second position to simultaneously rotate the drive wheel in a clockwise direction and the idler wheel in the opposite counterclockwise direction. With the drive wheel and idler wheel in firm contact with the flexible catheter, the simultaneous rotation of the drive wheel and idler wheel may distally advance (e.g., drive, extend, etc.) the flexible catheter of the first endoscopic instrument within the working channel of the endoscope, and thereby distally actuate the exposed suturing needle (FIG. 5B), e.g., to puncture/penetrate a tissue of the body passage. The lever may then be moved from the second position to the first position to simultaneously rotate the drive wheel in a counterclockwise direction and the idler wheel in the opposite clockwise direction. With the drive wheel and idler wheel maintained in firm contact with the flexible catheter, the simultaneous rotation of the drive wheel and idler wheel may proximally retract (e.g., withdraw) the flexible catheter of the first endoscopic instrument within the working channel of the endoscope to proximally retract the exposed suturing needle (FIG. 5A). The lever may be repeatedly moved between the first and second positions (e.g., back-and-forth) to proximally advance and distally retract the exposed suturing needle 176 to suture/stich the tissue of the body passage. Referring to FIG. 5C, in one embodiment, a second endoscopic instrument 182 (e.g., tissue grasper) may extend through the lumen of a tubular member 180 extending alongside an outer surface of the endoscope. As discussed above, the second endoscopic instrument 182 and tubular member 180 may be attached to the respective first and second attachment points of the control handle such that a single user may simultaneously manipulate the first endoscopic instrument with the lever and/or guide of the control handle using one hand and the second endoscopic instrument using the other hand. Additional features of the first endoscopic instrument may be found in Boston Scientific's co-pending U.S. patent application Ser. No. 15/901,477 entitled SUTURE BASED CLOSURE DEVICE, which application was filed on Feb. 21, 2018, and is hereby incorporated by reference herein in its entirety.

Figure 6:
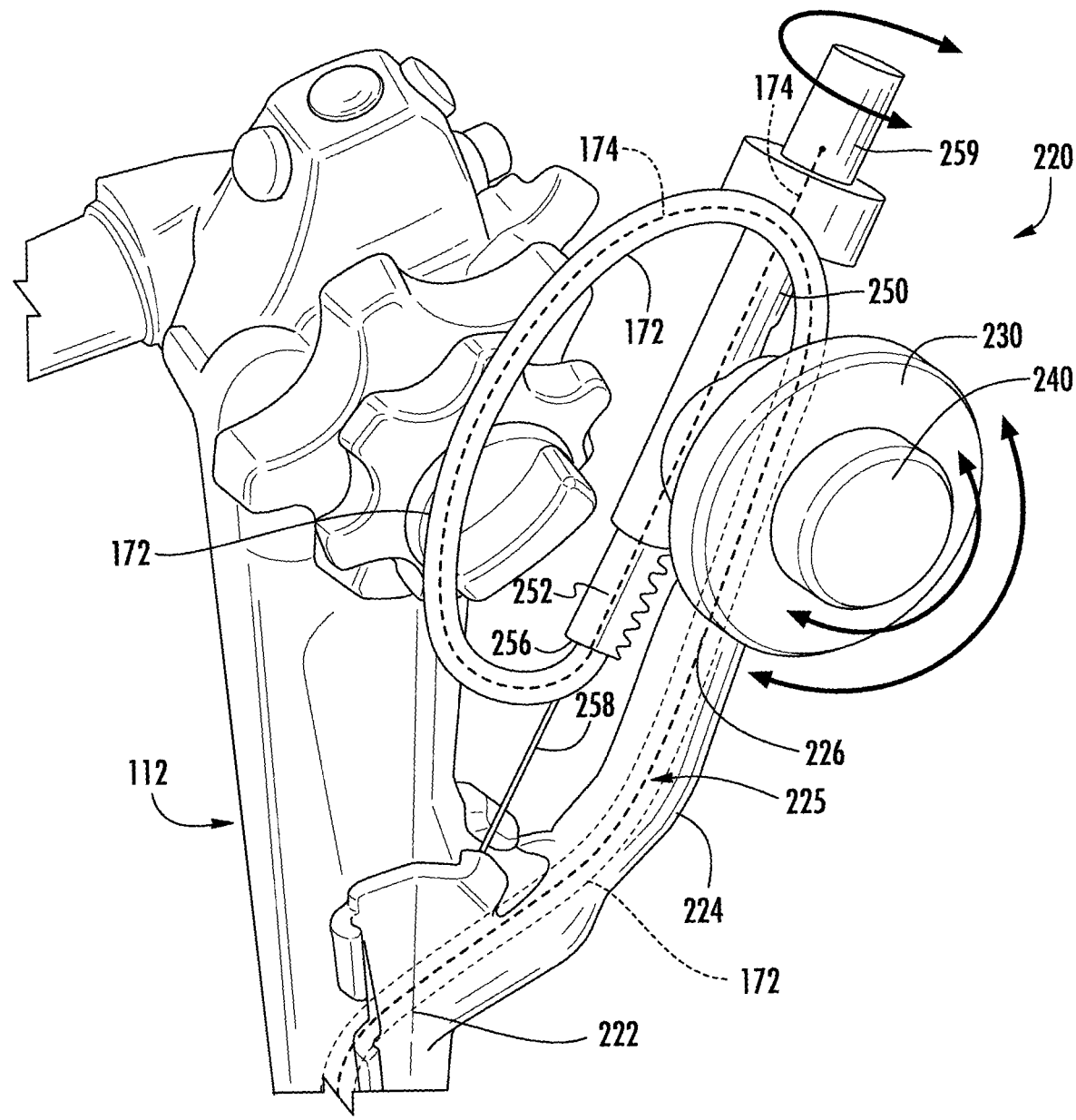
FIG. 6 provides a perspective view of a control handle, according to one embodiment of the present disclosure.

Referring to FIG. 6, in one embodiment, a control handle 220 of the present disclosure may include an adapter 222 (e.g., grip attachment) configured to reversibly (e.g., removably, releasably, etc.) attach to an outer surface of an endoscope handle 112 (e.g., grip). The control handle 220 may include a shaft 224 attached to (e.g., integrally formed with, connected to, etc.) the adapter. The adapter 222 may include a channel (e.g., opening) configured to receive (e.g., accommodate, fit over, etc.) a biopsy port and/or biopsy cap of the endoscope handle 112 (as discussed above). A lumen 225 may extend through a full length of the shaft 224 to receive a proximal portion of a first endoscopic instrument 170 therethrough. A first wheel 230 (e.g., large/inner wheel) and a second wheel 240 (e.g., small/outer wheel) may be rotatably attached to a proximal end 226 of the shaft 224 and a housing 250 may be attached to the proximal end 226 of the shaft 224 opposite the first and second wheels 230, 240. A linear gear 252 may be slidably/movably disposed within housing 250.

In one embodiment, a proximal portion of a first endoscopic instrument 170 may extend through the lumen 225 of the shaft 224 and the biopsy port into the working channel of the endoscope handle 112. The first endoscopic instrument may include a flexible catheter 172 defining a lumen and a control wire 174 movably/slidably disposed within the lumen through a full length of the flexible catheter 172. As discussed above, a suturing device (not shown) comprising a shuttle, sleeve and suturing needle may be disposed at a distal end of the first endoscopic instrument 170. The control wire 174 may be moved proximally and distally within the flexible catheter 172 such that movement of the sleeve in a proximal direction exposes the suturing needle from within the sleeve, and movement of the sleeve in a distal direction covers the suturing needle within the sleeve.

In various embodiments, a drive wheel and idler wheel (not shown) may be rotatably disposed (e.g., housed) within the control handle and configured to firmly contact opposite sides of the flexible catheter, (as discussed above). Referring to FIGS. 7A-7B, in one embodiment, the first wheel 230 may include an inner surface 238 and an outer surface 239. A post 232 comprising a polygonal outer surface 234 (e.g., hexagonal, heptagonal, octagonal, etc.) may extend from the inner surface 238 and a lumen 236 may extend through the post 232 to the outer surface 239 of the first wheel 230. The polygonal outer surface may be configured to contact a corresponding polygonal surface (not shown) of the drive wheel such that the first wheel 230 may be rotated in a first direction (e.g., clockwise) to simultaneously rotate the drive wheel in a first direction (e.g., counterclockwise) and the idler wheel in a second direction opposite the first direction (e.g., clockwise). The first wheel 230 may also be rotated in a second direction (e.g., counterclockwise) to simultaneously rotate the drive wheel in a second direction (e.g., clockwise) and the idler wheel in a first direction opposite the second direction (e.g., counterclockwise).

Referring to FIGS. 8A-8B, in one embodiment, the second wheel 240 may include an inner surface 248 and an outer surface 249. A tab 242 defining an opening 244 may extend from the inner surface 248 of the second wheel 240. The tab 242 may include a substantially circular outer surface configured to be rotatably disposed within the lumen 236 extending through the outer surface 239 of the first wheel 230. The opening 244 of the tab 242 may include a non-spherical shape (e.g., a curved portion and a flat portion) to receive the keyed end of a pinion shaft 260 (as discussed below).

Referring to FIG. 9, in one embodiment, the first and second wheels 230, 240 may be rotatably attached to the proximal end 226 of the shaft 224 by a pinion shaft 260. The pinion shaft 260 may include a substantially round portion 262, a keyed end 264 (e.g., a curved portion and a flat portion) and a pinion gear 266 configured to extend into the housing 250 and engage (e.g., mate or interlock with) the corresponding teeth of the linear gear 252. In one embodiment, the pinion shaft 260 may extend through the lumen 236 of the first wheel 230 and into the tab 242 of the second wheel 240 such that the substantially round portion 262 of the pinion shaft 260 is disposed within the lumen 236 of the first wheel 230 and the keyed end 264 extends into the opening 244 of the second wheel 240. With the inner surface 248 of the second wheel 240 in contact with or directly adjacent to the outer surface 239 of the first wheel 230, the first wheel 230 may be rotated in a first direction (e.g., clockwise) and a second direction (e.g., counterclockwise) around the substantially round portion 262 of the pinion shaft 260 independent of the second wheel 240. In addition, the second wheel 240 may be rotated in a first direction (e.g., clockwise) and second direction (e.g., counterclockwise) such that the substantially round portion 262 and pinion gear 266 of the pinion shaft 260 rotate in a corresponding first or second direction independent of the first wheel 230.

Referring again to FIG. 6, in one embodiment, a distal end 256 of the linear gear 252 may be attached to the proximal end of the flexible catheter 172, and a proximal portion of the flexible catheter 172 may form a loop to extend from the distal end of the linear gear 252 into/through the lumen 225 of the shaft 224. A proximal portion of the control wire 174 may extend through the housing 250 and the linear gear 252 and a proximal end of the control wire 174 may be connected to a dial or knob 259 at the proximal end of the housing 250. The dial or knob 259 may include a threaded inner surface configured to engage corresponding threaded grooves on an outer surface of the proximal end the housing 250. The dial or knob 259 may be rotated in a first direction (e.g., clockwise) or second direction (e.g., counterclockwise) to move the control wire 174 proximally or distally and in turn move the linear gear 252 proximally or distally along the housing 250. For example, the dial or knob 259 may be rotated in the first direction to move the linear gear 252 towards the proximal end of the housing 250, and the dial or knob 259 may be rotated in the second direction to move the linear gear 252 towards the distal end of the housing 250. In various embodiments, the starting position of the linear gear 252 along the housing 250 may be varied to move the sleeve 178 (e.g., attached to the distal end of the control wire 174) relative to the flexible catheter 172 (e.g., attached to the shuttle 179 of the suturing device 175) to adjust a position of the sleeve 178 relative to the suturing needle 176 (as discussed above). The starting position of the linear gear 252 along the housing 250 may be varied based on the body passage to be navigated by the endoscope and first endoscopic instrument such that the suturing needle 176 remains covered/protected by the sleeve (e.g., is not exposed) as the flexible catheter bends. With the position of the linear gear 252 set, and the distal end of the first endoscopic instrument positioned at or near the portion of the body passage to be manipulated, the second wheel 240 may be rotated (e.g., in the first direction) to distally extend the linear gear 252, and the control wire 174 attached thereto, to extend the flexible catheter 172 relative to the control handle 220. For example, as the linear gear 252 is extended the flexible catheter 172 may "pull" against the control wire 174 to pull the sleeve 178 proximally relative to the flexible catheter 172 to unlock (e.g., expose) the suturing needle 176. The second wheel 240 may also be rotated (e.g., in the second direction) to proximally retract the linear gear 252, and control wire 174 attached thereto, to lock (e.g., cover) the suturing needle 176 within the sleeve 178.

In use and by way of example, with the suturing needle of the first endoscopic instrument in the locked position (e.g., the sleeve distally extended over the suturing needle), the first endoscopic instrument may be advanced through the working channel of the endoscope and/or manipulated (e.g., maneuvered, repositioned, etc.) within a body passage of a patient. Referring again to FIGS. 5A-5C, the linear gear 252 may then be distally extended to expose the suturing needle 176 at the end of the first endoscopic instrument (FIG. 5A). The first wheel may then be rotated in a first direction to simultaneously rotate the drive wheel in a clockwise direction and the idler wheel in the opposite counterclockwise direction. With the drive wheel and idler wheel in firm contact with the flexible catheter, the simultaneous rotation of the drive wheel and idler wheel may distally advance (e.g., drive, extend, etc.) the first endoscopic instrument within the working channel of the endoscope, and thereby distally actuate the exposed suturing needle (FIG. 5B), e.g., to puncture/penetrate a tissue of the body passage. The first wheel may then be rotated in a second direction to simultaneously rotate the drive wheel in a counterclockwise direction and the idler wheel in the opposite clockwise direction. With the drive wheel and idler wheel maintained in firm contact with the flexible catheter, the simultaneous rotation of the drive wheel and idler wheel may proximally retract (e.g., withdraw) the first endoscopic instrument within the working channel of the endoscope to proximally retract the exposed suturing needle (FIG. 5A). The first wheel may be repeatedly rotated between the first and second directions to distally advance and proximally retract the exposed suturing needle 176 to suture/stich the tissue of the body passage.

Figure 10A:
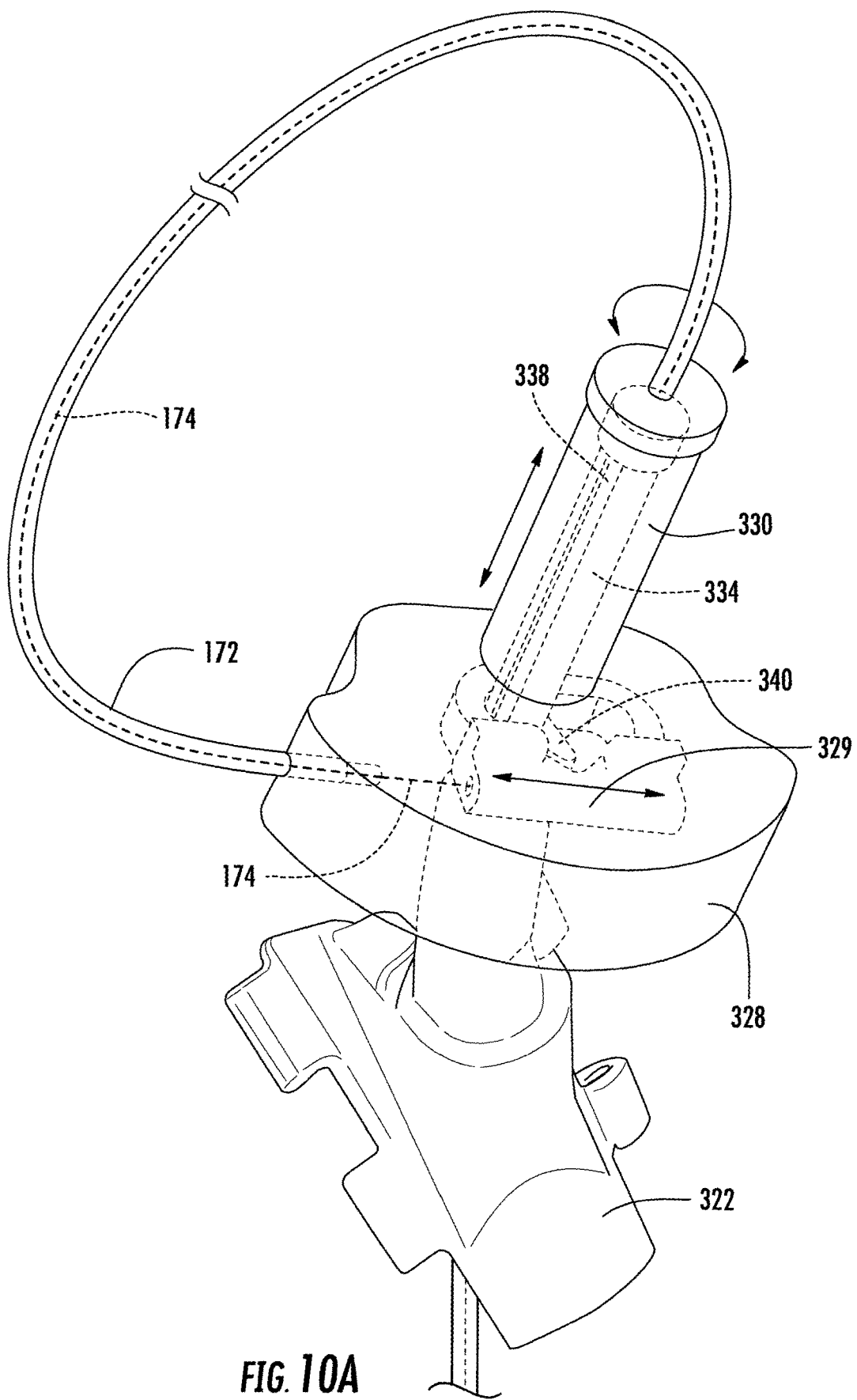
FIGS. 10A-10B provide perspective views of a control handle, according to one embodiment of the present disclosure.
Figure 10B:
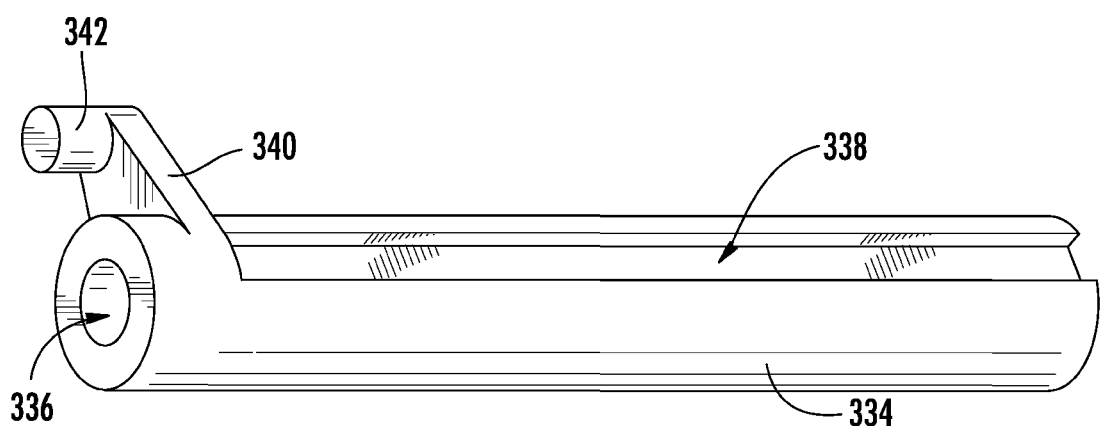

Referring to FIG. 10A, in one embodiment, a control handle 320 of the present disclosure may include an adapter 322 (e.g., grip attachment) configured to reversibly (e.g., removably, releasably, etc.) attach to an outer surface of an endoscope handle 112 (e.g., grip attachment). The adapter may include a channel (not shown) configured to receive (e.g., accommodate, fit over, etc.) a biopsy port and/or biopsy cap of the endoscope handle 112 (as discussed above). In various embodiments, the control handle 320 may include a shaft 324 attached to (e.g., integrally formed with, connected to, etc.) the adapter 322. A proximal end of the shaft 324 may be attached to (e.g., integrally formed with, connected to, etc.) a first surface (e.g., bottom surface) of a base 328. An inner post 334 may extend through an opening formed within a second surface (e.g., top surface) of the base 328. A lumen 336 may extend through a full length of the inner post 334 (FIG. 10B) to substantially align with a corresponding lumen 326 extending through a full length of the shaft 324. An outer surface of the inner post 334 may include a groove 338 extending along a portion of a length of the inner post. An arm 340 may extend outwardly from a distal end of the inner post, and a tab 342 may extend from a surface (e.g., bottom surface) of the arm 340 and substantially parallel to a distal portion of the inner post 334. The arm 340 may engage (e.g., extend into, etc.) a housing 329 slidably/movably disposed within the base 328. An outer post 330 may be slidably disposed over the inner post 334. A proximal end of the outer post 330 may include an opening 332 configured to substantially align with the lumen 336 of the inner post and/or firmly engage or grip an outer surface of the flexible catheter 172 extending therethrough (as discussed below). An elevated or raised ridge (not shown) may be formed along all or a portion of an inner surface of the outer post 330 to engage the corresponding groove 338 of the inner post 334 in an interlocking or keyed-fit configuration. The keyed-fit interaction may allow the outer post 330 to move proximally and distally relative to (e.g., slide along) the inner post 334 without imparting any corresponding proximal or distal movement to the inner post 334. The keyed-fit interaction may also allow the outer post 330 to be rotated in a first direction (e.g., clockwise) and a second direction (e.g., counterclockwise) such that the inner post 334 rotates in a corresponding first or second direction along with the outer post 330 to move the housing 329 (e.g., back-and-forth) within the base 328.

In one embodiment, a proximal end of the flexible catheter 172 may be attached to a sidewall of the base 328, and a proximal portion of the flexible catheter 172 may form a loop to extend from the base 328 into/through the opening 332 of the outer post 330, through the respective lumens 336, 326 of the inner post 334 and shaft 324 and into a working channel of the endoscope. A proximal portion of the control wire 174 may extend through an opening in the sidewall of the base 328 and a proximal end of the control wire 174 may be connected to the housing 329. The outer and inner posts 330, 334 may be rotated in the first direction or second direction to move the housing 329 within the base 328 and in turn move the control wire 174 proximally or distally within the flexible catheter 172. As discussed above, a suturing device (not shown) comprising a shuttle, sleeve and suturing needle may be disposed at a distal end of the first endoscopic instrument 170. The control wire 174 may be moved proximally and distally within the flexible catheter 172 such that movement of the sleeve in a proximal direction exposes the suturing needle from within the sleeve, and movement of the sleeve in a distal direction covers the suturing needle within the sleeve. Alternatively, the flexible catheter 172 may be attached to the housing 329 and the control wire 174 may be attached to the base 328 such that the flexible catheter may "pull" against the control wire 174 to pull the sleeve 178 proximally, as discussed above.

In use and by way of example, with the suturing needle of the first endoscopic instrument in the locked position (e.g., the sleeve distally extended over the suturing needle), the first endoscopic instrument may be advanced through the working channel of the endoscope and/or manipulated (e.g., maneuvered, repositioned, etc.) within a body passage of a patient. Referring again to FIGS. 5A-5C, the outer post may be rotated in the first direction to expose the suturing needle 176 at the end of the first endoscopic instrument (FIG. 5A). The outer post 330 may be moved distally (e.g., depressed, pushed down) along the inner post 334 to distally advance the flexible catheter 172 and distally actuate the exposed suturing needle (FIG. 5B), e.g., to puncture/penetrate a tissue of the body passage. The outer post may then be moved proximally (e.g., retracted, pulled up) to proximally retract the flexible catheter 172 and proximally withdrawn the exposed suturing needle. The outer post 330 may be repeatedly depressed and retracted to distally advance and proximally retract the exposed suturing needle 176 to suture/stitch the tissue of the body passage.

Although the present disclosure is directed towards an embodiment in which the tab 152 or second wheel 240 are connected to the flexible catheter 172, in various embodiments the tab 152 or second wheel 240 may be connected to the control wire 174 and the flexible catheter 172 may be connected directly to the control handle 120, 220. The dial or knob 154 of FIGS. 1 and 2 (e.g., to which the control wire 174 would otherwise be attached) would be removed.

In various embodiments, any or all of the components of the control handles 120, 220, 320 disclosed herein may be formed from or otherwise include a variety of rigid thermoplastic polymers that are resistant to various disinfecting or sterilizing modalities (e.g., chemicals, radiation, U.V. light), including, for example, polycarbonate, ABS, nylon, glass-reinforced nylon, acetal acrylic, PEET, PEEK, Pebax, polypropylene and the like.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A control handle, comprising:
   an adapter configured to attach to an outer surface of an endoscope;
   a housing coupled to the adapter and comprising a drive wheel and an idler wheel;
   a lever pivotally mounted on the housing, the lever configured to move between a first position and a second position to rotate the drive wheel; and
   a guide movably disposed with respect to the housing, the guide comprising a shaft having a proximal end positioned outside and adjacent to the housing for grasping by a user adjacent the housing, and a distal end positioned within the housing proximal to the drive wheel and the idler wheel;
   wherein:
   a guide lumen extends through the shaft between the proximal and distal ends of the shaft, and the distal end of the shaft extends into the housing to be positioned adjacent the drive wheel and the idler wheel to substantially align the guide lumen with a space between the drive wheel and the idler wheel to direct an endoscopic instrument extending through the guide lumen out of the guide lumen and distal to the distal end of the shaft and into selective direct contact with the drive wheel;
   the drive wheel is pinned to a drive gear;
   the idler wheel is pinned to an idler gear;
   teeth of the drive gear mate with corresponding teeth of the idler gear;
   the idler wheel and idler gear are rotatably mounted on opposite sides of an idler; and
   the idler is spring-loaded within the housing.

2. The control handle of claim 1, wherein the adapter includes a curved inner surface configured to conform to the outer surface of the endoscope.

3. The control handle of claim 1, wherein the adapter includes one or more attachment elements configured to reversibly engage the outer surface of the endoscope.

4. The control handle of claim 1, wherein a proximal portion of the adapter includes a channel configured to receive a biopsy port of the endoscope.

5. The control handle of claim 1, wherein the adapter includes a first arm with a first attachment point, the first attachment point configured to receive an outer surface of an endoscopic instrument.

6. The control handle of claim 1, wherein the adapter includes a second arm with a second attachment point, the second attachment point configured to receive a proximal end of a tubular member.

7. The control handle of claim 1, wherein the lever and the drive wheel are mounted on a common pin so that moving the lever from the first position to the second position rotates the drive wheel in a first direction, and moving the lever from the second position to the first position rotates the drive wheel in the second direction.

8. The control handle of claim 1, wherein a distance between the drive wheel and the idler wheel is adjustable to move the drive wheel and the idler wheel between a locked distance and an unlocked distance greater than the locked distance.

9. The control handle of claim 1, wherein the guide is slidable to adjust a distance between the drive wheel and the idler wheel.

10. The control handle of claim 1, wherein the guide is operable to adjust a distance between the drive wheel and the idler wheel.

11. The control handle of claim 1, wherein the distal end of the shaft is movable to move the idler to move the drive wheel with respect to the idler wheel.

12. The control handle of claim 1, wherein the lever is mounted on an end of a pin about which the drive wheel is rotatable.

13. An endoscopic system, comprising:
a control handle attachable to a handle of an endoscope, the control handle comprising:
a housing comprising a drive wheel and an idler wheel;
a lever pivotally connected to the housing, the lever configured to move between a first position and a second position to rotate the drive wheel; and
a guide movably disposed with respect to the housing, the guide comprising a shaft and defining a guide lumen extending through the shaft;
the drive wheel is pinned to a drive gear;
the idler wheel is pinned to an idler gear;
teeth of the drive gear mate with corresponding teeth of the idler gear;
the idler wheel and idler gear are rotatably mounted on opposite sides of an idler; and
the idler is spring-loaded within the housing;
a first endoscopic instrument comprising:
a flexible catheter defining a lumen, a control wire movably disposed within the lumen of the flexible catheter; and
a device actuatable by the control wire and disposed at a distal end of the first endoscopic instrument;
wherein: the guide lumen is substantially aligned with a space between the drive wheel and the idler wheel to direct the first endoscopic instrument extending through the guide lumen out of the guide lumen and into selective contact with the drive wheel.

14. The endoscopic system of claim 13, wherein:
a proximal portion of the control wire extends beyond the proximal end of the flexible catheter and through the lever; and
a proximal end of the control wire is attached to a dial at a proximal end of the lever.

15. The endoscopic system of claim 14, wherein:
moving the lever from the first position to the second position rotates the drive wheel and the drive gear in a first direction and rotates the idler wheel and idler gear in a second direction; and
moving the lever from the second position to the first position rotates the drive wheel and the drive gear in the second direction and rotates the idler wheel and idler gear in the first direction.

16. The endoscopic system of claim 15, wherein:
the drive wheel and idler wheel contact opposite sides of the flexible catheter extending through the housing;
moving the lever from the first position to the second position distally advances the flexible catheter within the working channel of the endoscope; and
moving the lever from the second position to the first position proximally retracts the flexible catheter within the working channel of the endoscope.

17. The endoscopic system of claim 14, further comprising a tab slidably disposed along a length of the lever, wherein:
rotating the dial in a first direction distally advances the tab along the lever to distally advance the control wire within the flexible catheter; and
rotating the dial in a second direction proximally retracts the tab along the lever to proximally retract the control wire within the flexible catheter.

18. The endoscopic system of claim 17, further comprising a sleeve, wherein: the sleeve is proximally retracted relative to the flexible catheter as the control wire is distally extended within the flexible catheter; and the sleeve is distally advanced relative to the flexible catheter as the control wire is proximally retracted within the flexible catheter.

19. A control handle, comprising:
a housing comprising a drive wheel and an idler wheel;
a lever pivotally connected to the housing, the lever configured to move between a first position and a second position to rotate the drive wheel and the idler wheel; and
a guide movably disposed within the housing, the guide comprising a shaft and a lumen extending through the shaft;
wherein: the lumen substantially aligns with a space between the drive wheel and the idler wheel;
the drive wheel is pinned to a drive gear;
the idler wheel is pinned to an idler gear;
teeth of the drive gear mate with corresponding teeth of the idler gear;
the lever is pivotally connected to the drive wheel and the drive gear;
moving the lever from the first position to the second position rotates the drive wheel and the drive gear in a first direction and rotates the idler wheel and idler gear in a second direction;
moving the lever from the second position to the first position rotates the drive wheel and the drive gear in the second direction and rotates the idler wheel and idler gear in the first direction; and
the idler wheel and idler gear are rotatably mounted on opposite sides of an idler, wherein the idler is spring-loaded within the housing.

20. The control handle of claim 19, wherein a distance between the drive wheel and the idler wheel is adjustable to move the drive wheel and the idler wheel between a locked distance and an unlocked distance greater than the locked distance.

* * * * *